US00PP08858P

United States Patent [19]

Bloom

[11] Patent Number: Plant 8,858

[45] Date of Patent: Aug. 9, 1994

[54] HEUCHERA VARIETY CV. ABSI

[75] Inventor: Adrian J. R. Bloom, Diss, England

[73] Assignee: Blooms of Bressingham Ltd., Bressingham, England

[21] Appl. No.: 109,604

[22] Filed: Aug. 19, 1993

[51] Int. Cl.[5] ..... A01H 5/00

[52] U.S. Cl. ..... Plt./68.1

[58] Field of Search ..... Plt. 68.1

[56] References Cited

PUBLICATIONS

Bailey, L. H., "Heuchera" *The Standard Cyclopedia of Horticulture* 1935 The Macmillan & Co., Inc. pp. 1480 and 1481.

*Primary Examiner*—James R. Feyrer

*Attorney, Agent, or Firm*—Synnestvedt & Lechner

[57] ABSTRACT

A new and distinct variety of Heuchera plant that is characterized by its graceful flowers and especially by its decorative foliage consisting of large, distinctly lobed leaves which are strongly ribbed and which maintain a dark metallic purple-bronze color year round.

1 Drawing Sheet

BACKGROUND AND SUMMARY OF THE INVENTION

This invention relates to the discovery and asexual propagation of a new and distinct variety of Heuchera, a member of the Saxifragaceae family and commonly known as alumroot or coral-bells. The new plant was discovered by Adrian J. R. Bloom, as a mutant of the Heuchera americana species in a cultivated planting of Heuchera americana plants that were growing in the Blooms of Bressingham nursery in Bressingham, England. Seedlings were grown from seed collected from the parent species. From these seedlings, superior stock was then selected. The new Heuchera variety was discovered as a whole specimen and further superior stock was then propagated asexually. The new Heuchera variety was first propagated by Mr. Bloom in the same Bressingham nursery in 1986, and testing has shown that it maintains its distinguishing characteristics, as hereinafter set out, over several succeeding generations through asexual propagation using division, shoot cuttings and tissue culturing.

The new variety of Heuchera has been named 'Absi', and it is a hardy, herbaceous, summer-flowering perennial characterized by its graceful flowers and especially by its decorative foliage which stays dark metallic purple-bronze year round. 'Absi' may be distinguished from its parent, Heuchera americana, by the following combination of characteristics: the 'Absi' plant has larger leaves with a distinctively ribbed surface, and a distinctively bronze and glossy upper surface and bright purple lower surface. The leaves of the parent Heuchera americana are broad and begin as flushed and veined coppery brown, later becoming a glistening dark green with age. 'Absi' is particularly distinguishable from the variety it most closely resembles, Heuchera, 'Palace Purple', in that the color of its leaves is a much richer and deeper purple-bronze than that of the 'Palace Purple'. Heuchera 'Palace Purple' leaves are a metallic, coppery purple, the intensity of which varies from plant to plant. In addition, the 'Absi' has strongly ribbed leaves which are larger than those of 'Palace Purple'. Also, 'Palace Purple', unlike 'Absi', is unstable in commerce and often grown from seed, thereby resulting in much variance with regard to its foliage characteristics.

Due to its richly colored foliage and its delicate flowers, 'Absi' is useful for ground cover, rock gardens, and ornamental planting.

BRIEF DESCRIPTION OF THE FIGURES

The accompanying drawing illustrates the new Heuchera variety 'Absi' in full color as grown in Bressingham, England.

BOTANICAL DESCRIPTION OF THE PLANT

Figure 1:
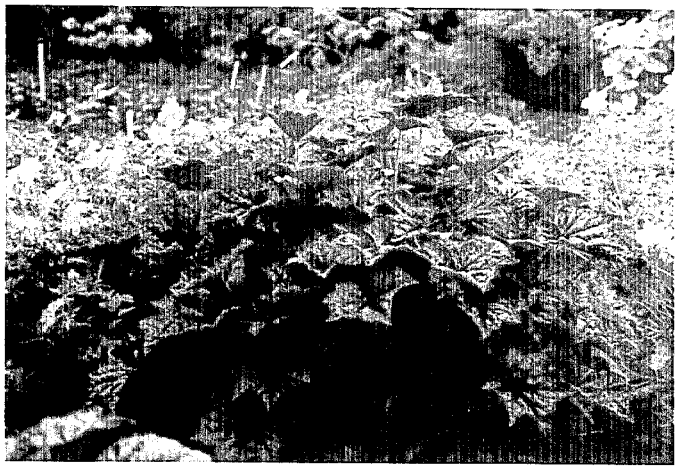
FIG. 1 is a photograph of the new 'Absi' variety, demonstrating the richly colored foliage of the new variety and, in particular, its large, lobed leaves which are distinctively ribbed and have a characteristic dark bronze upper surface and light purple lower surface. While the surface of the leaves appear in the photograph to be mottled with patterns of silver and purple, this aspect is merely due to the light reflecting off of the rugose, glossy upper surface of the leaves.

Throughout this specification, color names beginning with a small letter signify that the name of the color, as used in common speech, is aptly descriptive. Color names beginning with a capital letter designate values based on the R.H.S. Colour Chart published by the Royal Horticultural Society of London, England.

The descriptive matter which follows pertains to the 'Absi' variety of Heuchera grown in Bressingham, England in 1986, and is believed to apply to plants of the variety grown under similar conditions of soil and climate elsewhere.

Name: Heuchera cv. 'Absi'.

Parentage: A whole specimen mutation of Heuchera americana.

Size: Medium, about 30–50 cm wide and about 50 cm in height; scapes can stand about 20 cm above to give a total average height of about 70 cm.

Growth Habit: Slow, spreading into large tufts of petioled, lobed leaves forming a rounded mound; no propensity to branch; flower stems arise from a central crown which spreads laterally with age, at a slow rate.

Strength: Hardy outdoors.

Root system: Fibrous.

Flower stems:

*Color before flowering.*—Dark bronze (Greyed-Purple 186-A).

*Color at flowering time.*—Faded dark bronze (Grey-Brown 199-A).

*Type.*—Solid.

*Texture.*—Hairy.

*Girth.*—About 2 mm (maximum).

*Length.*—About 70 cm (maximum).

*Foliage.*—None present on flower stems.

Leaf stems:

*Length.*—About 10 cm.

*Strength.*—Strong, although wiry and slender.

*Color.*—Green, due to being shaded from the light.

*Texture.*—Hairy.

Foliage:

*Type.*—Herbaceous.

*Texture.*—Upper surface: hairy, glossy. Lower surface: hairy, rough.

*Color.*—Upper surface: Dark bronze (Greyed-Purple 186-A). Lower surface: Light purple (Red-Purple 71-A).

*Seasonal changes.*—The lower surface becomes more coppery with age, while the upper surface develops a dark bronze coloring progressively through the seasons until at its best, when it reaches maturity.

*Size.*—Length: about 15 cm. Breadth: about 13 cm.

*Shape.*—Lobed.

*Density.*—Abundant.

*Fragrance.*—Absent.

Inflorescence:

*Season.*—Mid-June to September.

*Duration.*—About 12 to 14 weeks.

*Habit.*—Continuous.

Flowers:

*Type.*—Single; panicle.

*Habit.*—Carried above the foliage.

*Size.*—About 2 mm.

*Borne.*—Tiny bell-shaped flowers, normally produced several together.

*Petals.*—Texture: smooth.

*Fragrance.*—Absent.

*Color.*—Pink (Red 49-C), shading down to ivory (White 155-A), with green (Green 138-A) spots at tip.

I claim:

1. A new and distinct variety of Heuchera plant called 'Absi' as herein illustrated and described.

* * * * *